United States Patent
Roets et al.

(10) Patent No.: US 11,679,040 B2
(45) Date of Patent: Jun. 20, 2023

(54) ABSORBENT CORE FOR DISPOSABLE ABSORBENT ARTICLES WITH INCREASED ABSORPTION RATE AND IMPROVED INTEGRITY

(71) Applicants: ONTEX BV, Buggenhout (BE); ONTEX GROUP NV, Erembodegem (BE)

(72) Inventors: Karen Roets, San Pedro Cholula Puebla (MX); Christel Mailinger, Elz (DE); Thomas Heege, Düngenheim (DE)

(73) Assignees: ONTEX BV, Buggenhout (BE); ONTEX GROUP NV, Erembodegem (BE)

( * ) Notice: Subject to any disclaimer, the term of this patent is extended or adjusted under 35 U.S.C. 154(b) by 0 days.

(21) Appl. No.: 17/787,032

(22) PCT Filed: Dec. 18, 2020

(86) PCT No.: PCT/EP2020/087098
§ 371 (c)(1),
(2) Date: Jun. 17, 2022

(87) PCT Pub. No.: WO2021/123221
PCT Pub. Date: Jun. 24, 2021

(65) Prior Publication Data
US 2023/0081440 A1    Mar. 16, 2023

(30) Foreign Application Priority Data
Dec. 20, 2019  (EP) ..................... 19219034

(51) Int. Cl.
*A61F 13/15* (2006.01)
*A61F 13/532* (2006.01)
(Continued)

(52) U.S. Cl.
CPC .... *A61F 13/5323* (2013.01); *A61F 13/49007* (2013.01); *A61F 13/539* (2013.01);
(Continued)

(58) Field of Classification Search
CPC ........... A61F 13/5323; A61F 13/49007; A61F 13/539; A61F 13/530007; A61F 13/536; A61F 13/534
See application file for complete search history.

(56) References Cited

U.S. PATENT DOCUMENTS

| 7,718,021 B2 | 5/2010 | Venturino et al. |
| 8,198,506 B2 | 6/2012 | Venturino et al. |
| (Continued) | | |

FOREIGN PATENT DOCUMENTS

| EP | 3238676 A1 | 11/2017 | |
| EP | 3403627 A1 * | 11/2018 | ....... A61F 13/00987 |

OTHER PUBLICATIONS

International Search Report and Written Opinion for PCT/EP2020/087098, dated Apr. 7, 2021.

*Primary Examiner* — Jacqueline F Stephens
(74) *Attorney, Agent, or Firm* — Vivicar Law, PLLC

(57) ABSTRACT

The present disclosure invention relates to a disposable absorbent article (100) comprising a liquid-pervious topsheet (10), a liquid-impervious backsheet (20) and an absorbent assembly (30) between the topsheet (10) and the backsheet (20). The absorbent assembly (30) comprises an absorbent core (40), an upper core wrap (50) and a lower core wrap (60). The absorbent core (40) comprises at least two cavities (70) free of absorbent material wherein the upper core wrap (50) and the lower core wrap (60) are permanently attached to each other, said cavities (70) being interconnected via at least one connecting line (80) comprising absorbent material. The absorbent core (40) has a first basis weight in the zone out of the cavities (70) and the connecting lines (80) and a second basis weight in the connecting lines (80), the first basis weight being greater than the second basis weight. in the cavities (70). The (Continued)

resulting absorbent assembly (30) may show all together a very good integrity, a very good distribution of fluids and a quick rate of absorption.

12 Claims, 11 Drawing Sheets

(51) Int. Cl.
*A61F 13/539* (2006.01)
*A61F 13/49* (2006.01)
A61F 13/53 (2006.01)

(52) U.S. Cl.
CPC ............. *A61F 2013/530007* (2013.01); *A61F 2013/530496* (2013.01)

(56) References Cited

U.S. PATENT DOCUMENTS

| | | |
|---|---|---|
| 9,789,009 B2 | 10/2017 | Joseph |
| 10,052,242 B2 | 8/2018 | Bianchi et al. |
| 10,071,002 B2 | 9/2018 | Bianchi et al. |
| 10,130,527 B2 | 11/2018 | Peri et al. |
| 10,137,039 B2 | 11/2018 | Stelzig et al. |
| 10,335,324 B2 | 7/2019 | Roe et al. |
| 2006/0058761 A1 | 3/2006 | Kudo et al. |
| 2015/0080821 A1 | 3/2015 | Peri et al. |
| 2015/0342796 A1 | 12/2015 | Bianchi et al. |
| 2017/0135871 A1 | 5/2017 | Kamphus |
| 2018/0360671 A1 | 12/2018 | Joseph |

\* cited by examiner

ABSORBENT CORE FOR DISPOSABLE ABSORBENT ARTICLES WITH INCREASED ABSORPTION RATE AND IMPROVED INTEGRITY

CROSS-REFERENCE TO RELATED APPLICATIONS

This application is the national stage application of corresponding international application number PCT/EP2020/087098, filed Dec. 18, 2020, which claims priority to and the benefit of European application no. 19219034.6, filed Dec. 20, 2019, which is hereby incorporated by reference in its entirety.

FIELD OF THE INVENTION

This disclosure pertains to the technical field of disposable absorbent articles such as sanitary napkins, panty liners, baby diapers, baby pants, adult diapers, adult pants, adult incontinence pads, etc., having an absorbent assembly with improved integrity, lower return of liquids to the surface (rewet), improved distribution of fluids and a quick rate of absorption.

BACKGROUND

The disposable absorbent articles are articles which are used in proximity with the skin of a wearer to absorb and retain body exudates; they are basically constituted by an upper liquid-pervious topsheet, a bottom liquid impervious backsheet and an absorbent core disposed between them. The absorbent core of this kind of articles is generally composed of fibers of absorbent material and/or particles of superabsorbent material; its main functions are to absorb and to retain liquid or semi-liquid exudates from the human body that penetrate through the upper layer of the article. For the absorbent core being effective, it needs to have a good integrity, that is to say, the absorbent core must maintain its structure and does not break or collapse either in a dry or in a wet state. If said absorbent core breaks, its absorption and retention capacity is lost and it is not capable of distributing the fluids properly causing leakage, agglomerations of absorbent material and discomfort to the wearer. Multiple attempts have been made to prevent or minimize the structural breaks of the absorbent cores such as the use of nets, adhesives, core wraps, embossing and others. On the other hand, for an absorbent core having a good functionality, the fluids must be distributed properly along it in order to use its full absorbent capacity; it is also relevant that the fluids penetrate into the absorbent core as quickly as possible in order to preserve the health of the skin of the wearer.

There are some patents focused on improving the integrity of the absorbent cores, for example the U.S. Pat. Nos. 8,198,506 and 7,718,021 (Kimberly Clark Worldwide Inc.) which disclose a stabilized absorbent composite web and the method for producing it; said absorbent composite comprises a first sheet joined to a second sheet through a plurality of holes formed in the absorbent core. These patents are fully focused on improving the integrity of the absorbent core sacrificing the ability to absorb liquids more quickly as well as the ability to distribute them more evenly and efficiently through the absorbent core.

On the other hand, there are several patents focused in improving the distribution of fluids in the absorbent core using channels. For example the patents listed below refer to absorbent articles comprising an absorbent core with an upper core wrap, a lower core wrap, a fibrous layer and one or more areas free of absorbent material through which the upper core wrap joins to the lower core wrap, such that when the absorbent material swells, the core wrap forms channels along the areas free of absorbent material; these channels also help for having a good rate of absorption of fluids into the core: U.S. Pat. Nos. 10,071,002, 10,130,527, 9,789,009, 10,137,039, 10,335,324, 10,052,242, US 2018 0360671, US 2017 0135871, US 2015 0080821.

There are some other patents referring to absorbent cores free of cellulose fibers which improve the containment and retention capacity of the core, as for example US20150342796A1 from Procter & Gamble which refers to an absorbent core comprising a core wrap enclosing superabsorbent particles: the superabsorbent particles form a pattern of dot-shape discrete areas which can be oriented longitudinally or transversely; these areas are separated from each other by areas substantially free of material and could also contain channels free of absorbent material. Absorbent cores as the one described in the referred patent application are difficult to produce and are not soft enough for being comfortable to the user.

Other patents referring to absorbent cores divulge the use of zones with different basis weight and density within the core. Depending the way these zones are disposed, they are used for different purposes. For example, EP3238676B1 (Procter & Gamble) describes an absorbent core with first and second longitudinal channels free of absorbent material; the core may further comprise one or more transverse oriented folding lines in which the basis weight of absorbent material reaches a minimum relative to the immediately adjacent regions. These zones with lower basis weight are used only for facilitating the folding and as they reach the longitudinal sides of the core, could also facilitate the flow of fluid promoting the run-off of liquid.

The present invention addresses the technical problems described above and provides an absorbent article with an absorbent assembly with improved integrity which also improves the absorption rate, the rewet and the distribution of fluids inside it, expressed as the percentage of use of the absorbent core, said absorbent article having the features of claim 1. The at least one connecting line participates for improving the distribution of fluids in the absorbent core. By combining in an absorbent assembly (i) the cavities substantially free of absorbent material, (ii) the at least one connecting line interconnecting the cavities and having absorbent material with a lower basis weight than the rest of the core (as taken outside of the cavities) and (iii) the permanent bonding between the upper and lower core wraps, the resulting absorbent assembly may show all together a very good integrity, a very good distribution of fluids, a quick rate of absorption and a low rewet.

SUMMARY OF THE INVENTION

The present invention relates to a disposable absorbent article having a longitudinal direction and a transverse direction, the absorbent article comprising a liquid-pervious topsheet, a liquid-impervious backsheet and an absorbent assembly disposed between the topsheet and the backsheet. The absorbent assembly has two longitudinal edges, two transverse edges, a wearer-facing surface, a garment-facing surface, a longitudinal central axis extending along a length of the absorbent assembly and a transverse central axis defining a front portion and a back portion. The absorbent assembly comprises an absorbent core, an upper core wrap and a lower core wrap. The absorbent core comprises absorbent material comprised by a mixture of superabsorbent polymer and cellulosic fibers. It further comprises at least two cavities free of absorbent material having a width with respect to the transverse central axis and a length with respect to the longitudinal central axis. Said cavities are interconnected via at least one connecting line having a width with respect to the transverse central axis and a length with respect to the longitudinal central axis. The at least one connecting line comprises absorbent material. The absorbent core has a first basis weight in the zone out of the cavities and the connecting lines and a second basis weight in the connecting lines, the first basis weight being greater than the second basis weight. The upper core wrap and the lower core wrap are permanently attached to each other in the cavities.

In an embodiment of the invention, the at least two cavities of the absorbent core may be aligned on the longitudinal central axis of the absorbent assembly and be interconnected via at least one longitudinal connecting line substantially parallel to the longitudinal central axis. In an alternative embodiment of the invention, the cavities of the absorbent core may form a pattern comprising two rows of at least two cavities, the cavities of each row being longitudinally interconnected via at least one longitudinal connecting line substantially parallel to the longitudinal central axis, each row being disposed on each side of the longitudinal central axis. Both these patterns may provide particularly advantageous integrity, distribution of fluids and quick rate of absorption.

DETAILED DESCRIPTION OF THE INVENTION

Figure 1:
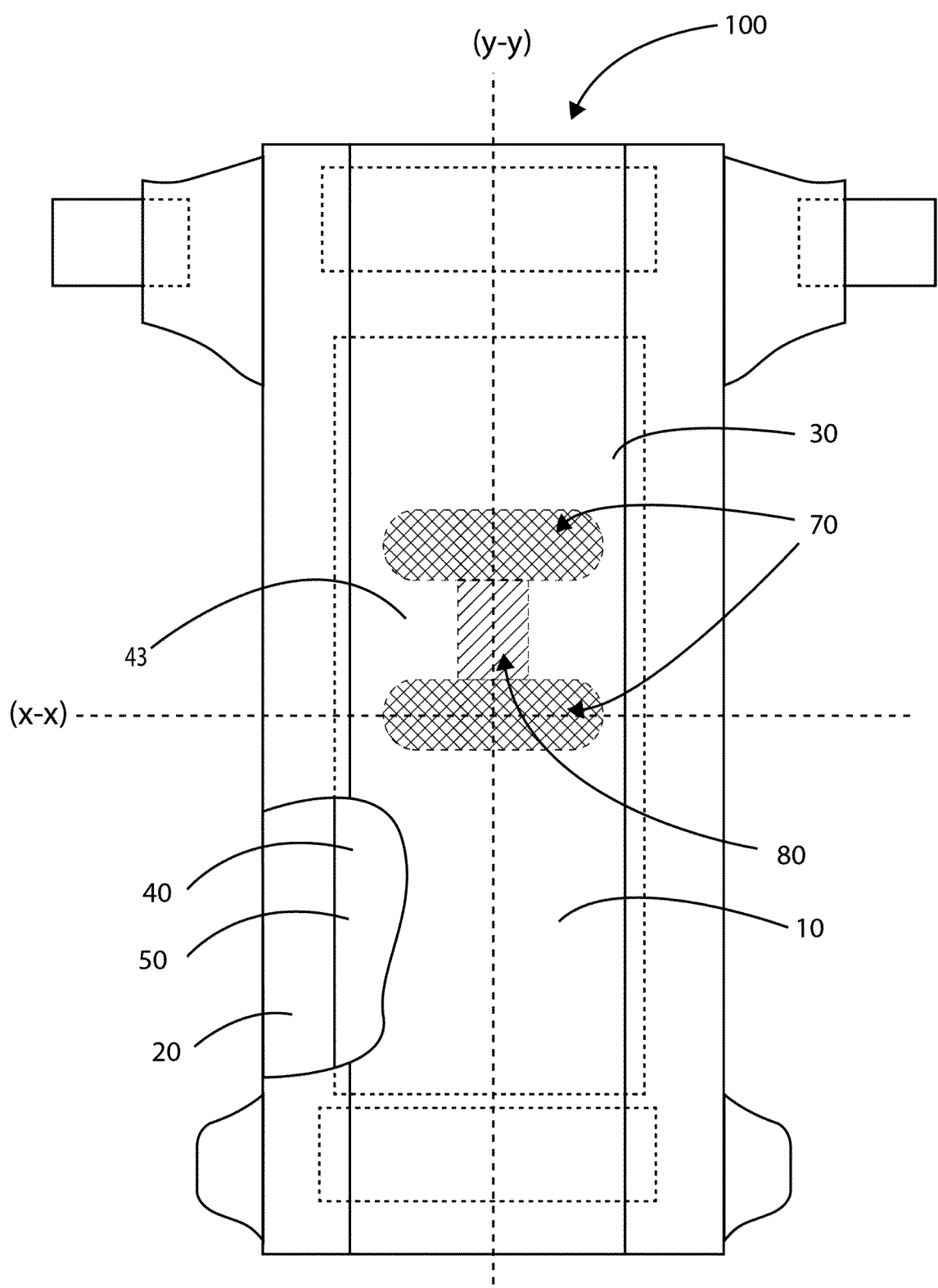
FIG. 1 shows a plan view of the wearer facing surface of a disposable absorbent article according to the present invention in an extended configuration.

All the terms used to define the elements and/or features of the present invention, including technical and scientific terms, have the meaning as commonly understood by one of ordinary skill in the art to which this invention belongs.

As used herein, the following terms have the following meanings:

"Absorbent articles" refers to devices that absorb and contain body exudates, and, more specifically, refers to devices that are placed against or in proximity to the body of the wearer to absorb and contain the various exudates discharged from the body. Absorbent articles include baby and adult diapers, baby and adult pants, adult incontinence undergarments, feminine hygiene products, and the like.

"Topsheet" refers to a liquid permeable substrate forming the inner cover of the absorbent article and which in use is placed in direct contact with the skin of the wearer. The topsheet can comprise a nonwoven material made of natural or synthetic fibers or any mixture of natural or synthetic fibers and made by any method known in the art.

"Backsheet" refers to a liquid impermeable sheet forming the garment facing surface of the absorbent article. The backsheet prevents body fluids and exudates absorbed by the absorbent article for passing through it. The backsheet may comprise a thin plastic film such as a thermoplastic film (e.g. a polyethylene or polypropylene film) or it could be a laminate comprised by a thin impermeable film and a nonwoven web. The materials which are commonly used as backsheets may include breathable materials which permit vapors to pass through it still preventing, fluids for passing through the backsheet.

"Absorbent assembly" refers to the combination of an absorbent core enclosed by at least one core wrap.

"Core wrap" refers to one or more substrate layers that enclose the absorbent core and can comprise one or more layers of nonwoven material made of mono or bicomponent natural or synthetic fibers such as, but not limited to polyester, polyethylene, polypropylene, viscose, rayon, cotton, polyhydroxyalkanoates, etc., they may comprise hydrophilic and/or hydrophobic treatments.

"Absorbent core" refers to a structure for the absorption and containment of body exudates, said absorbent core is comprised by absorbent materials such as, but not limited to cellulosic fluff pulp, tissue layers, superabsorbent polymer particles (SAP), absorbent foam materials, absorbent nonwoven materials or mixtures thereof; the absorbent core can have any shape as for example a rectangular shape, an anatomical shape, an hourglass-shape, a "T" shape or any other one known in the art.

"Cavities" refers to areas substantially free of absorbent material located in the absorbent core.

"Connecting lines" refers to substantially rectilinear regions that interconnect at least two cavities to each other. Contrary to the cavities, the connecting lines contain some absorbent material having a lower basis weight than the rest of the absorbent core.

"Attached" refers to the relationship between two or more elements, which can be joined to each other in any known way, such as but not limited to ultrasonic bonding, mechanical bonding, thermal bonding, by adhesives, or the like.

Embodiments of articles according to the present invention will now be described, from here on, in relation to a disposable diaper, but it is understood that the absorbent article may be selected from disposable diapers, disposable adult pants, disposable baby pants, adult incontinence pads, sanitary napkins and the like. The technical features described in one or more embodiments may be combined with one or more other embodiments without departing from the intention of the disclosure and without generalization thereof.

FIG. 1 illustrates a wearer facing surface of a disposable absorbent article (100) according to an embodiment of the present invention in an extended configuration. As can be seen, the disposable absorbent article (100) comprises basically a liquid-pervious topsheet (10), a liquid-impervious backsheet (20) and an absorbent assembly (30) placed between them. The disposable absorbent article comprises two opposite longitudinal sides and two opposite transverse sides; the disposable absorbent article (100) can also contain a fastening system, leg and waist elastic zones, front and back ears, transfer layers, containment barriers and other elements well known in the art.

Figure 1A:
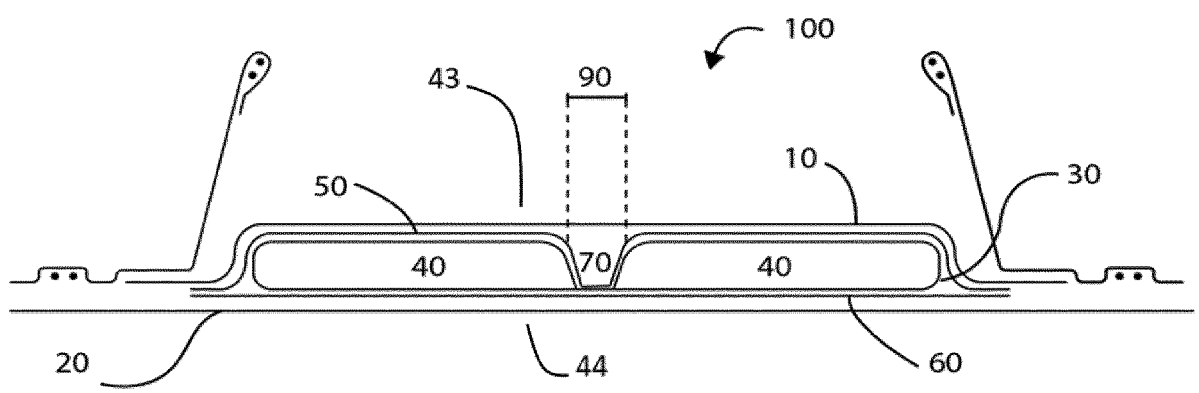
FIG. 1A is a cross-sectional view of the disposable absorbent article of FIG. 1 taken along the transverse central axis (X-X).

FIG. 1A shows a transverse cross-section of the disposable absorbent article of FIG. 1 taken along the transverse central axis (X-X). The disposable absorbent article (100) comprises a liquid-pervious topsheet (10), an absorbent assembly (30) and a backsheet (20); the absorbent assembly (30) is constituted by an upper core wrap (50), an absorbent core (40) and a lower core wrap (60).

The absorbent assembly (30) has two longitudinal edges (41, 41'), two transverse edges (42, 42'), a wearer-facing surface (43), a garment-facing surface (44), a longitudinal central axis (Y-Y) and a transverse central axis (X-X). The longitudinal central axis (Y-Y) extends along the length of the absorbent assembly (30) so that it defines a left side and a right side, each one of said sides having a substantially equal transverse width; the transverse central axis (X-X) extends along the width of the absorbent assembly (30) defining a front portion (45) and a back portion (46), each one of said portions having a substantially equal length. The absorbent core (40) of the invention comprises at least two cavities (70) and at least one connecting line (80) interconnecting them.

Said absorbent core (40) is comprised of absorbent material which is composed preferably of a mixture of superabsorbent polymer particles (SAP) and cellulosic fibers which could be replaced by other fibers of absorbent material of natural or synthetic origin. The superabsorbent polymer particles are able to absorb and retain fluids many times their own weight and may be in the form of particles, fibers, flakes or the like.

Figure 2:
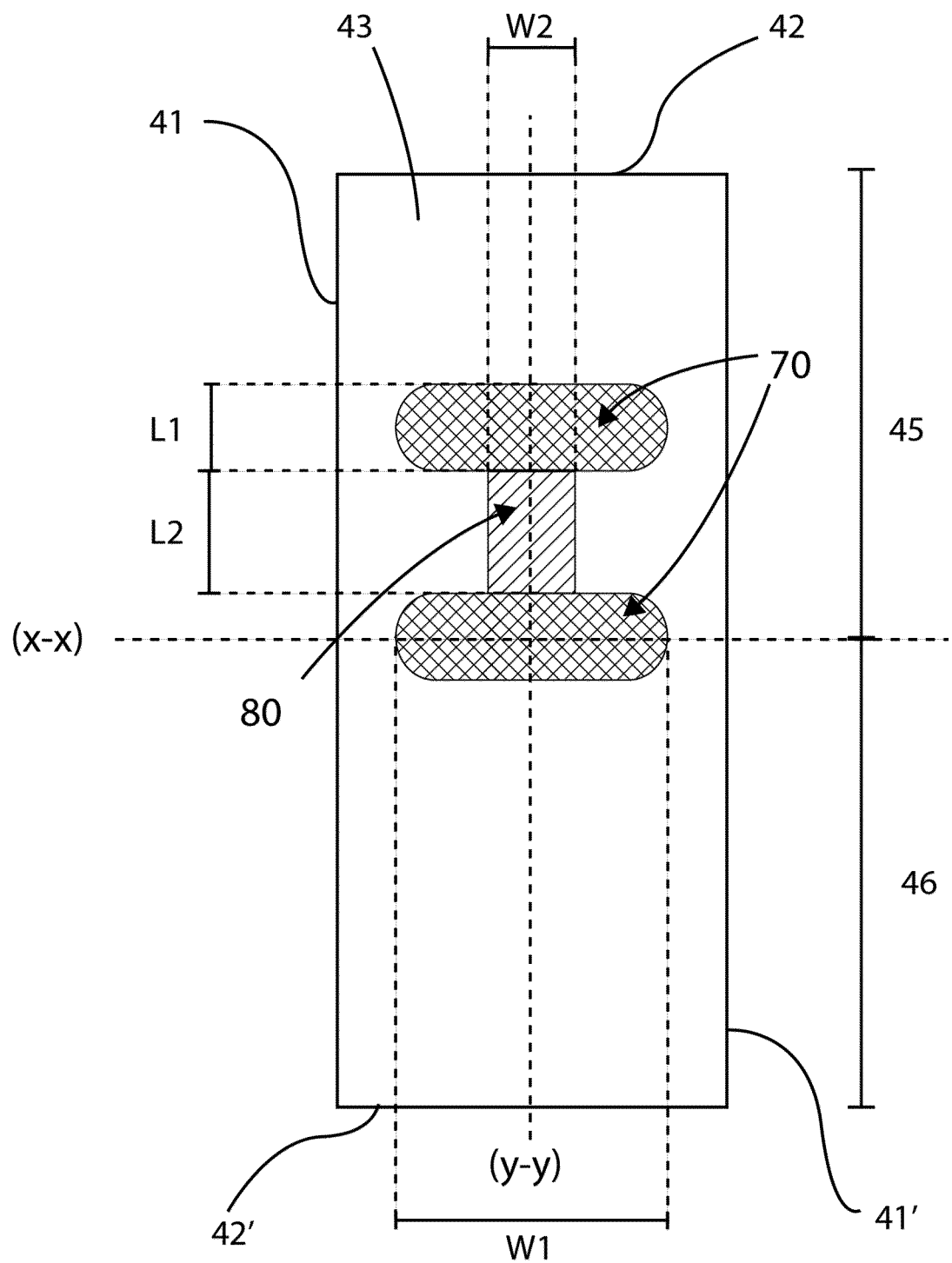
FIG. 2 representatively illustrates a plan view of the absorbent assembly of a disposable absorbent article according to an embodiment of the present invention.

The cavities (70), as are shown for example in FIG. 2, are areas substantially free of absorbent material and have a width (W1) in transverse direction and a length (L1) in longitudinal direction. The cavities (70) may contain a minimum quantity of absorbent material, mainly because of some contamination during the manufacturing process.

Advantageously, cavities according to the invention may have an area between 50 mm$^2$ and 2500 mm$^2$, preferably between 100 mm$^2$ and 2000 mm$^2$, more preferably between 150 mm$^2$ and 1500 mm$^2$.

Preferably, the cavities (70) of the invention are longitudinally spaced from each other by a distance between 5 mm and 250 mm, more preferably between 10 mm and 200 mm, even more preferably between 10 mm and 150 mm or between 15 mm and 150 mm. Advantageously, they are transversely spaced from each other by a distance between 5 mm and 250 mm, more preferably between 10 mm and 200 mm, even more preferably between 10 mm and 150 mm or between 15 mm and 150 mm. These distances between the cavities corresponds to the shortest distance between the perimeter of one cavity and the perimeter of the next cavity in longitudinal or transverse direction. The distance in longitudinal direction between two neighboring cavities (70) may correspond to the length (L2) of a connecting line (80).

In a preferred embodiment, the cavities (70) have a circular shape but alternatively, they may have a shape selected from the group consisting of triangles, squares, rectangles, polygons, ovals, semicircles, arrows, crosses, irregular shapes and combinations thereof.

As the upper and lower core wraps are permanently attached in these cavities, the absorbent material between each cavity is immobilized thereby helping in maintaining the integrity of the absorbent core (40). These dimensions and shapes have proven to help in providing this integrity.

One function of the at least one connecting line (80) is to spread or distribute the fluids effectively throughout the absorbent core (40), thereby helping in increasing the absorption rate and better using all the absorption capacity of the absorbent core. Each connecting line has a width (W2) with respect to the transverse direction and a length (L2) with respect to the longitudinal direction, as can be seen in FIG. 2. The ratio (W2/W1) between the transverse width of the connecting line (W2) and the transverse width of the cavities substantially free of absorbent material (W1) is preferably at most 1, more preferably at most 0.9, even more preferably at most 0.8, so that when a fluid reaches a cavity, it passes quickly through the connecting line(s) directly to another cavity helping in distributing the fluid in the absorbent core.

The absorbent core (40) of the present invention has a first basis weight (bw1) outside the cavities (70) and the connecting line (80), and a second basis weight (bw2) in the connecting line (80). The first basis weight (bw1) is greater than the second basis weight (bw2). Preferably, the ratio (bw2/bw1) between the second basis weight (bw2) and the first basis weight (bw1) is between 0.25 and 0.95, more preferably between 0.35 and 0.85, even more preferably between 0.45 and 0.75. These ratios are advantageous in that the fluid may be transported more quickly in the areas having less basis weight. For this reason, the distribution of fluid inside the absorbent core (40) of the present invention may be improved compared with the distribution of fluids in an absorbent core (40) having a constant basis weight. In addition, as the fluid is better distributed, it does not accumulate in small zones and as a result of this, the rewet may be lowered. On the other side, the cavities (70) in conjunction with the connecting line (80) may help for the absorbent assembly (30) having a fast rate of absorption and/or in directing the fluid in order to use all the absorption capacity of the core (40).

Figure 2A:
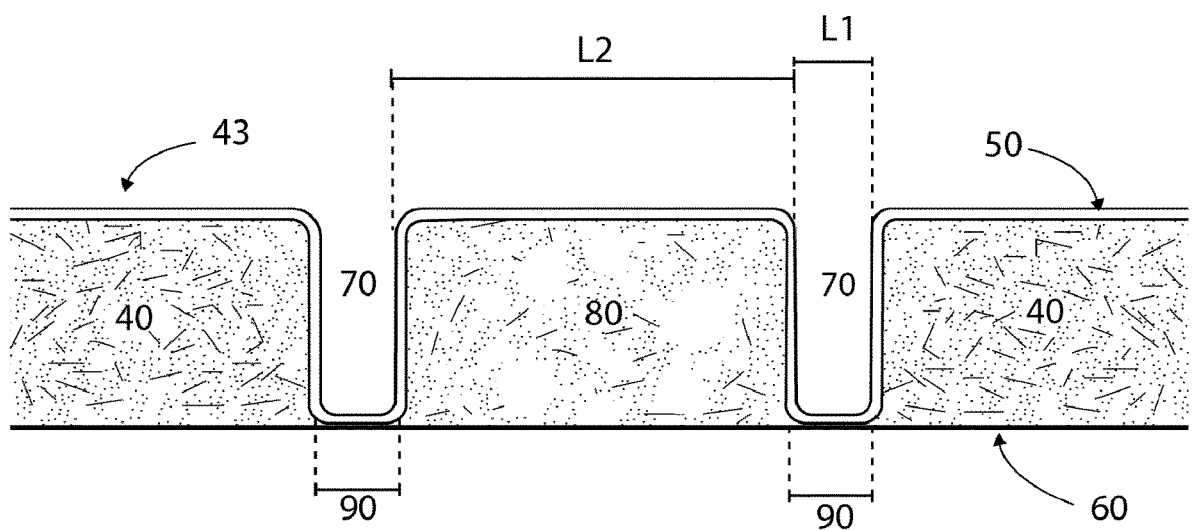
FIG. 2a is a longitudinal cross-sectional view of the absorbent assembly of FIG. 2 taken along the longitudinal central axis (Y-Y)

In preferred embodiments of the present invention, the upper core wrap (50) is permanently attached to the lower core wrap (60) in the cavities (70) by means of adhesive, thermal bonding, pressure bonding, mechanical bonding, ultrasonic bonding or combinations thereof or any other means known in the art. The permanent attachment between the upper core wrap (50) and the lower core wrap (60) in the cavities (70) defines bonding zones (90), as can be seen in FIG. 2a which may contribute to the absorbent assembly (30) having a very good integrity given that the absorbent material is immobilized between the cavities (70). The upper core wrap and lower core wrap (50, 60) are preferably nonwoven webs made from natural or synthetic fibers and/or combinations thereof; they can be composed of one or more layers bonded together and can be manufactured by any known method. The upper core wrap (50) is preferably a hydrophilic nonwoven web having a basis weight between 5 g/m$^2$ and 20 g/m$^2$. The lower core wrap (60) could be a hydrophobic or a hydrophilic nonwoven web having a basis weight between about 5 g/m$^2$ and 20 g/m$^2$.

Figure 3:
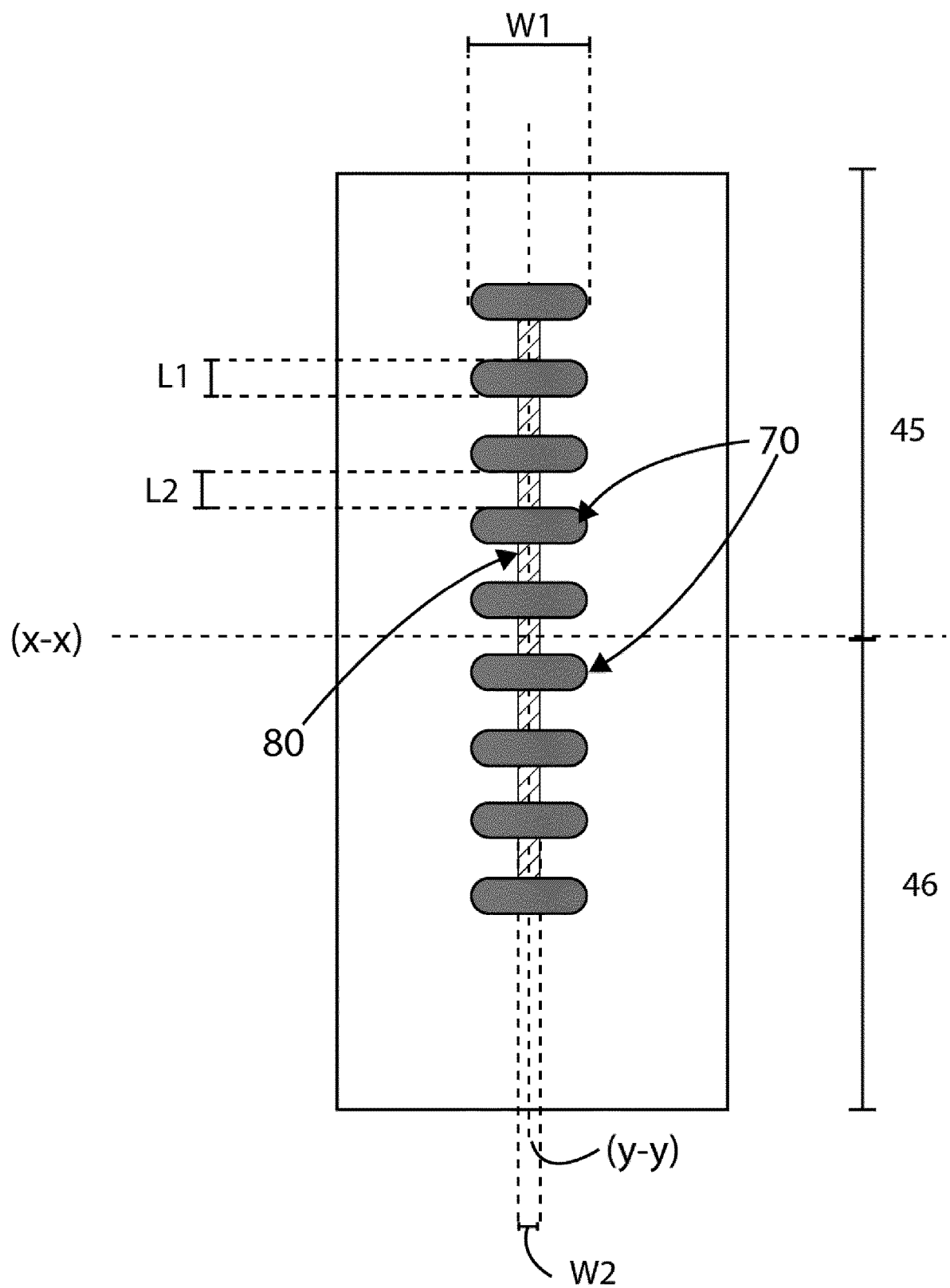
FIG. 3 Illustrates a plan view of an absorbent assembly of a disposable absorbent article according to an embodiment of the present invention.

In an embodiment of the present invention shown in FIG. 3, nine cavities (70) are aligned on the longitudinal central axis (Y-Y) of the absorbent assembly (30), and are interconnected via at least eight longitudinal connecting lines (80), said connecting lines (80) being on the longitudinal central axis (Y-Y).

Figure 4:
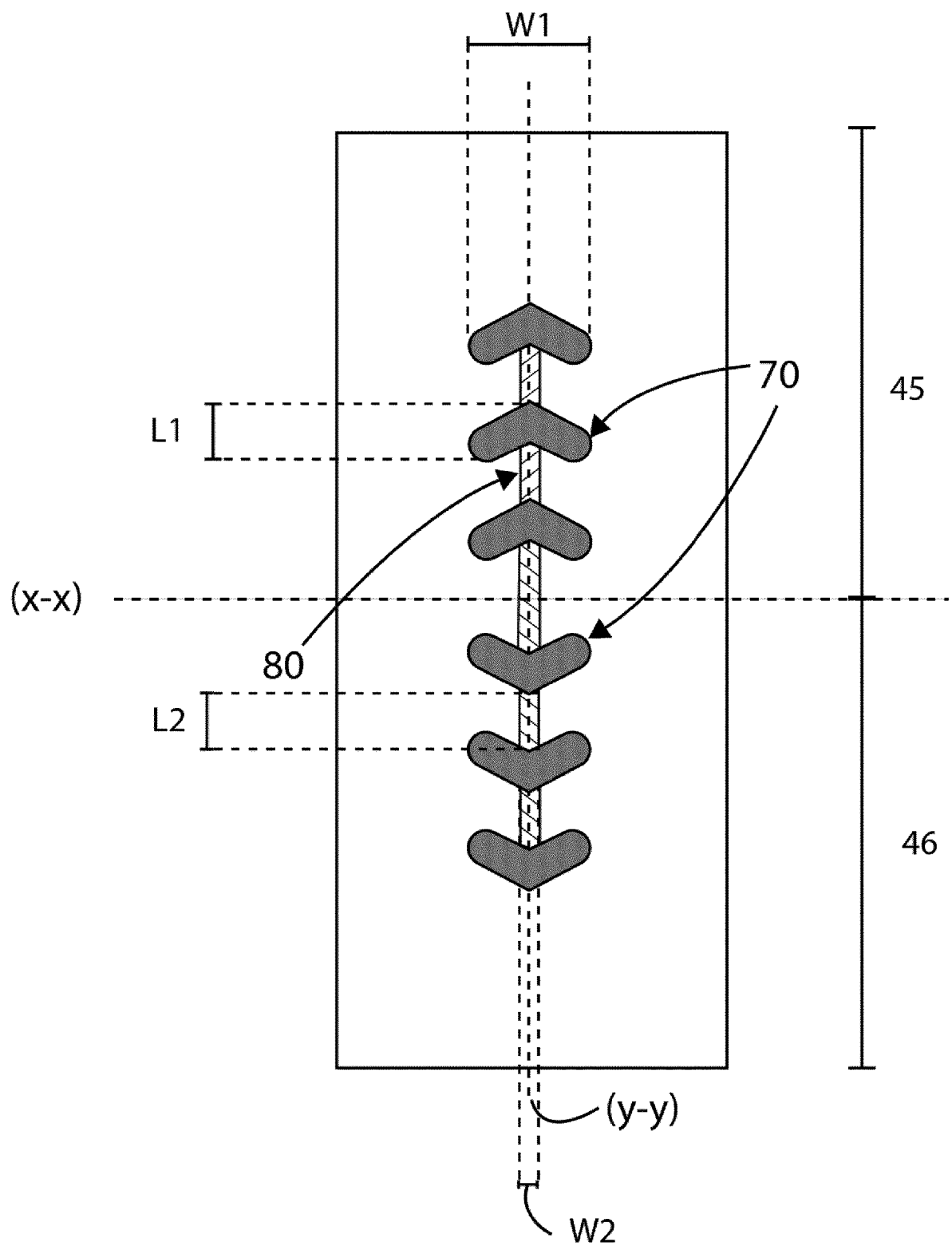
FIG. 4 shows a plan view of another embodiment of the absorbent assembly of a disposable absorbent article according to the present invention.

Another embodiment of the present invention is shown in FIG. 4. In this embodiment, six cavities (70) have an arrow-shape and are aligned on the longitudinal central axis of the absorbent assembly (30), such that, the arrow-shaped cavities (70) point toward the transverse edges of the absorbent assembly (30). Said cavities (70) are interconnected through five longitudinal connection lines (80) on the longitudinal central axis (Y-Y).

Figure 5:
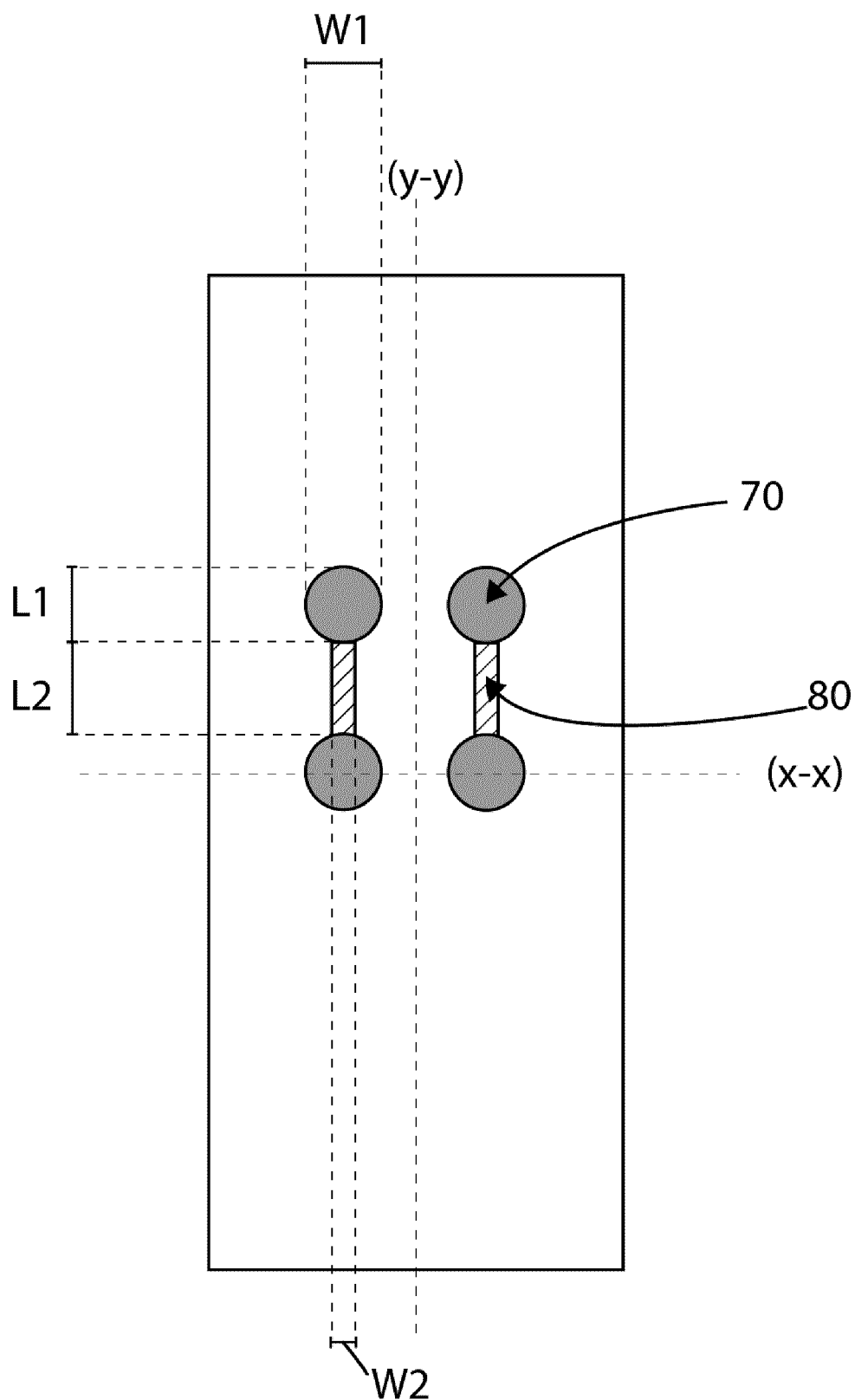
FIGS. 5, 6, 7 and 8 show plan views of other embodiments of the absorbent assembly of disposable absorbent articles according to the present invention.

FIG. 5 shows another embodiment of the present invention in which the cavities (70) are disposed in the absorbent core (40) forming a pattern, said pattern comprising two rows of two cavities (70) being interconnected via one longitudinal connecting lines (80). Each row is disposed on each side of the longitudinal central axis (Y-Y) of the absorbent assembly (30) and parallel to it. The connecting lines (80) are substantially parallel to the longitudinal central axis (Y-Y).

Figure 6:
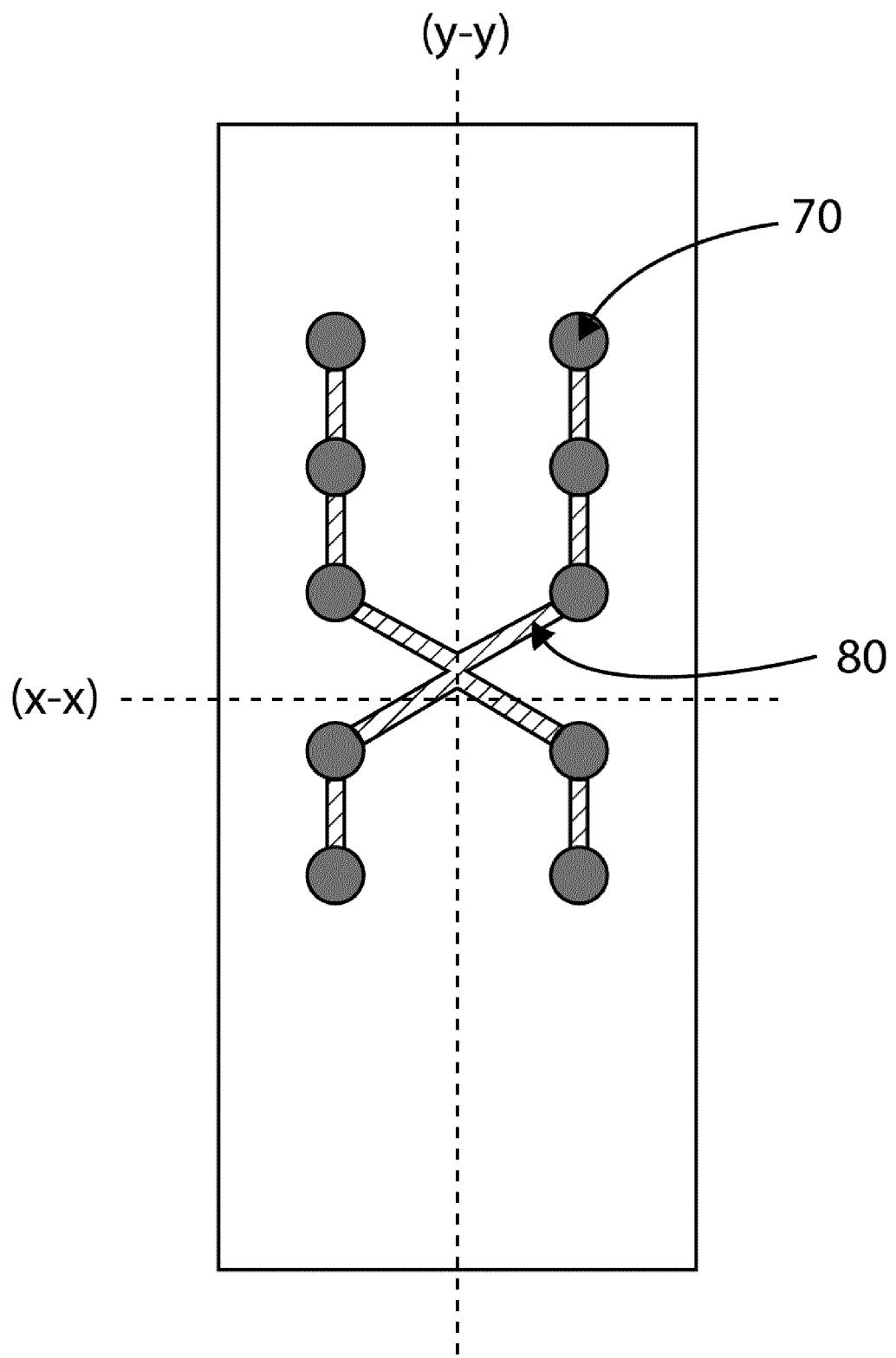

FIG. 6 shows another embodiment of the present invention in which the cavities (70) form a pattern comprising four rows. Each row comprises at least two cavities (70) interconnected via at least one connecting line (80), one row being disposed in the front right quarter of the absorbent assembly (30), the second one being disposed in the front left quarter of the absorbent assembly (30), the third one in the back right quarter of the absorbent assembly (30) and the fourth row in the back left quarter of the absorbent assembly (30) respectively. The first row is interconnected to the fourth row via at least one connecting line (80) and the second row is interconnected to the third row via at least one connecting line (80), such that, these connecting lines (80) form an X-shaped pattern.

Figure 7:
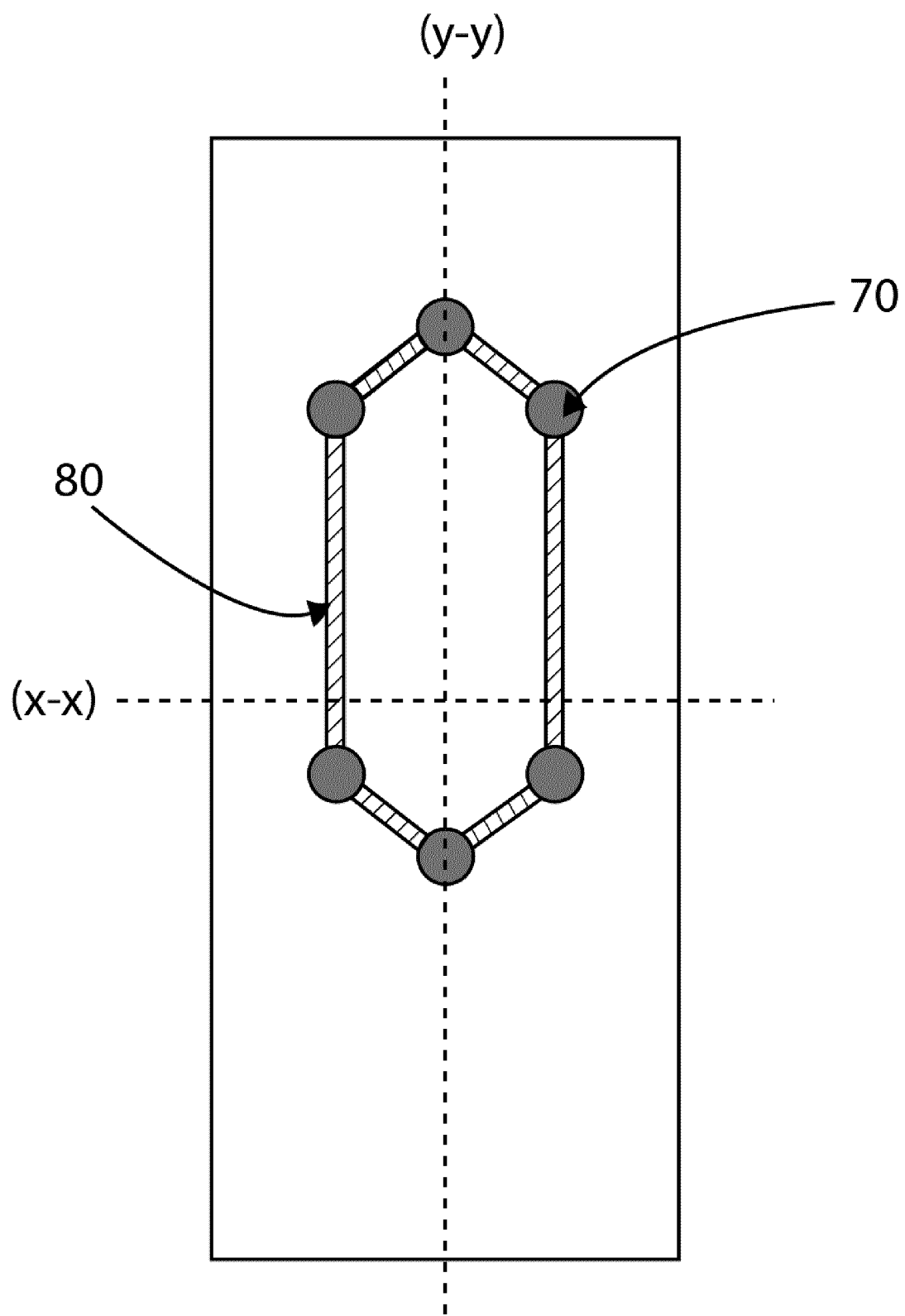

FIG. 7 shows another embodiment of the present invention in which, the cavities (70) are disposed in the absorbent core (40) forming a hexagonal pattern, said hexagonal pattern comprising six cavities (70) coinciding with the apex of the hexagonal pattern, and a plurality of connecting lines (80) connecting the cavities (70) such that, the connecting lines (80) define the outer perimeter of the hexagonal pattern.

In some embodiments of the invention, one or more connecting lines (80) may comprise regions having the second basis weight (bw2) and other regions having a third basis weight (bw3), so that the first basis weight (bw1) is greater than the second basis weight (bw2), and the second basis weight (bw2) is greater than the third basis weight (bw3). In this way the fluid may run in the connecting lines at varying speed, helping the absorbent assembly (30) to be more efficient in the rate of absorption and in the distribution of fluids.

The cavities (70) may be distributed in the absorbent core forming any pattern. As the discharge of fluids into the absorbent article is made generally in the front portion (45) of the absorbent assembly (30), this front portion (45) is the one that tends to first loss the integrity, thereby losing its capability to absorb and distribute the fluids. Therefore, in a preferred embodiment, more than 50% of the total area of the cavities (70) is disposed in the front portion of the absorbent assembly (30). The total area of the cavities is obtained by adding the individual area of each cavity (70).

Test Methods
Rate of Absorption, Percentage of Use of the Absorbent Core and Rewet
Materials:
Synthetic urine (0.9% saline solution)
Universal support
Semi-analytical balance with precision of 0.01 g;
Calculator
Stopwatch
Metal scale
Separation funnel 125 mL (7 mL/s or equivalent);
Tissue paper previously cut to square 100 mm×100 mm;
Test tube 100 ml;
Stainless steel dosing ring (internal 0 53 mm/height 50 mm and wall thickness 3 mm);
Weight 2.5 kg (external 0 76 mm and height 70 mm);
Disposable absorbent articles
Separation funnel fitting ring with internal 0 55 mm
Procedure:
1. Prepare the synthetic urine.
2. Stack and weigh an amount of absorbent paper, according to the values measured in table 1.
3. Record the weight (Dry weight of the absorbent paper) to measure the fluid returns (first, second and third);
4. Measure the absorbent core length and record this length.
5. Cut and remove the leg elastics to keep the product taut. For underwear, tear the side seal of the product and use scissors to cut the outline of the polyethylene film. Then position/stick the product with the outer side on an acrylic plate with hook strips at the ends to keep the product straight.
6. Mark the insult zone in the disposable absorbent article (drawing an horizontal line on the frontal portion of the disposable absorbent article at a distance of 5.0 cm to the transverse central axis (X-X) and position the dosing ring over the horizontal line and aligned with the longitudinal central axis (Y-Y). The zone inside the dosing ring is the insult zone.
7. For each disposable absorbent article/size analyzed, measure an amount of synthetic urine (showed in Table 2, Table 3) and place it in the funnel.
8. Place the tip of the funnel about 1.0 cm from the top end of the dosing ring.
9. Open the funnel valve and start the timer when the liquid contacts the product, stop the timer as soon as all the synthetic urine is absorbed and record the time as the primary acquisition time (first time).
10. Once all synthetic urine has been absorbed, wait 10 minutes and place the previously weighed 15.0 g absorbent paper stack centered over the marked area of insult, put the 2.50 kg weight on the absorbent paper stack and wait for 2 minutes. Mark the point at the front and back portions of the absorbent core as far as the liquid went, measure the length of the stain created by the synthetic urine, record the length as the primary fluid distribution (first distribution).
11. After 2 minutes, remove the weight of 2.50 kg, weigh and record the weight of the absorbent paper stack (wet weight);
12. Repeat the previous steps to measure the second and third return, distribution and time. (The laboratory test must be carried out with 5 different samples, then the values obtained are averaged in order to have a reliable result.)

Return (g)=Weight of the absorbent paper (g)−Dry weight of the absorbent paper (g)

Rate of absorption (ml/s)=Amount of synthetic urine (ml)/time of absorption (s).

Total distribution (mm)=Third measured length of the stain (mm).

Percentage of use of the absorbent core=[Total distribution (mm)*100]/Length of the core (mm)

Preparation of the Synthetic Urine
2 L volumetric flask;
Coloring;
Sodium chloride;
Deionized water.
Procedure:
1. Weigh 18 g of sodium chloride and transfer to a 2.0 L volumetric flask.
2. Dissolve and complete to volume with deionized water.
3. Add a small portion of coloring to the solution The saline solution should be prepared 4 hours before the test; its shelf life is up to 7 days.

Tables

TABLE 1

| Absorbent paper weight | |
| --- | --- |
| Primary Return | 15.0 g (+/−0.5 g) |
| Secondary Return | 30.0 g (+/−0.5 g) |
| Tertiary Return | 30.0 g (+/−0.5 g) |

TABLE 2

| Infants | | | | | | |
| --- | --- | --- | --- | --- | --- | --- |
| | Size | | | | | |
| | Newborn | Small | Medium | Large | XL | XXL |
| Quantity (ml.) | 40 | 40 | 60 | 80 | 100 | 100 |

TABLE 3

| Adults | | | | | |
| --- | --- | --- | --- | --- | --- |
| | Size | | | | |
| | Youth | Small | Medium | Large | XL |
| Quantity (ml.) | 40 | 40 | 60 | 80 | 100 |

EXAMPLES

Embodiment A (not according to the invention): Disposable absorbent baby diaper size "L" containing an absorbent assembly comprising:
- an upper core wrap and a lower core wrap having a basis weight of 8 g/m² each and
- an absorbent core without cavities and connecting lines containing 7 g of cellulosic fibers and 10.5 g of superabsorbent polymer (SAP) and having a basis weight (bw1) of 505.56 g/m².

Embodiment B (according to the invention): Disposable absorbent baby diaper size "L" containing an absorbent assembly comprising:
- an upper core wrap and a lower core wrap having a basis weight of 8 g/m² each one and
- an absorbent core containing 7 g of cellulosic fibers and 10.5 g of superabsorbent polymer (SAP) and having six bar shaped cavities (70) [each one with an area of around 306 mm²] aligned on the longitudinal central axis (Y-Y) interconnected via five longitudinal connecting lines (80). The absorbent core has a basis weight (bw1) of 397 g/m² and each one of the connecting lines has a basis weight (bw2) of 291.12 g/m².

Embodiment C (according to the invention): Disposable absorbent baby diaper size "L" containing an absorbent assembly comprising:
- an upper core wrap and a lower core wrap each one having a basis weight of 8 g/m² and
- an absorbent core containing 7 g of cellulosic fibers and 10.5 g of superabsorbent polymer (SAP) and having six arrow-shaped cavities (70) [each one with an area of around 378 mm²] aligned on the longitudinal central axis (Y-Y) interconnected via five longitudinal connecting lines (80). The absorbent core has a basis weight (bw1) of 557 g/m² and each one of the connecting lines has a basis weight (bw2) of 339 g/m².

Figure 8:
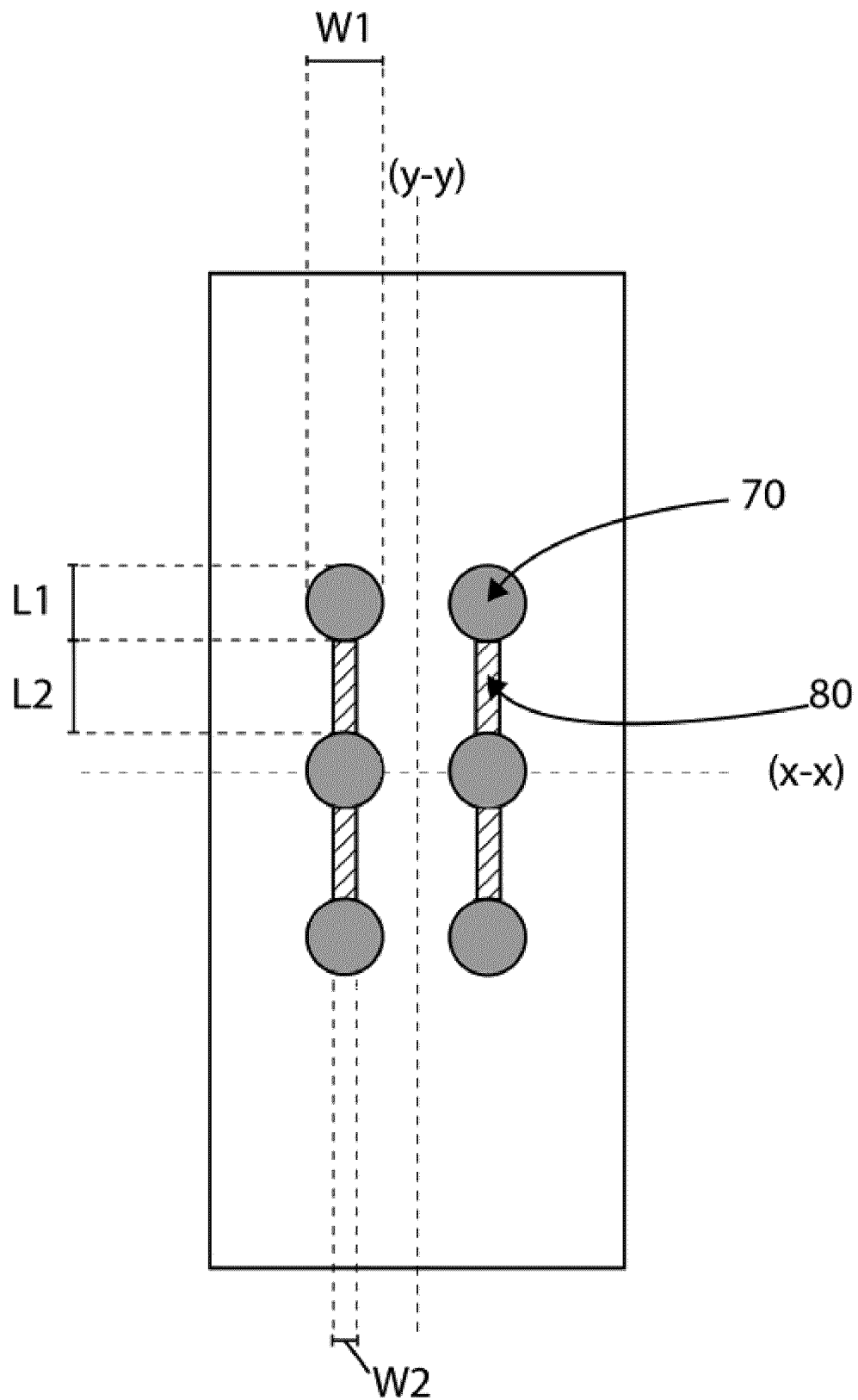

Embodiment D (according to the invention and as illustrated in FIG. 8): Disposable absorbent baby diaper size "L" containing an absorbent assembly comprising:
- an upper core wrap and a lower core wrap each one having a basis weight of 8 g/m² and
- an absorbent core containing 7 g of cellulosic fibers and 10.5 g of superabsorbent polymer (SAP) and having 2 rows of three dot-shaped cavities (70) [each dot-shaped cavity having an area of around 159 mm²], each row being disposed at each side of the longitudinal central axis (Y-Y), having 2 connecting lines (80) connecting the 3 cavities of each row. The absorbent core has a basis weight (bw1) of 557 g/m² and each one of the connecting lines has a basis weight (bw2) of 339 g/m².

Figure 9:
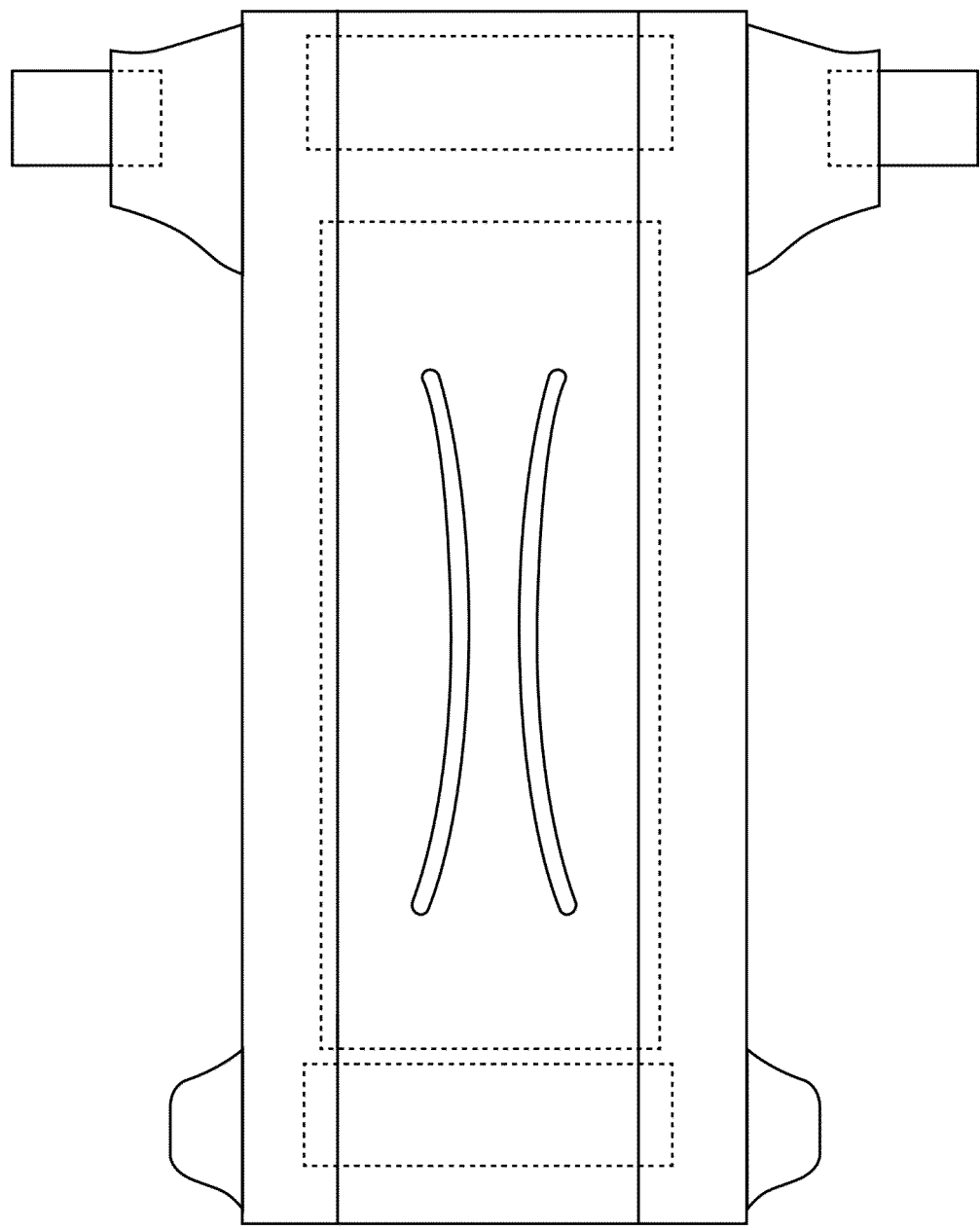
FIG. 9 shows a plan view of a disposable absorbent article of the prior art (channeled diaper).

Pampers Confort Sec® (as illustrated in FIG. 9) size "L" having an absorbent assembly comprising:
- an upper core having a basis weight of 9 g/m² and a lower core wrap having a basis weight of 12 g/m²; and
- an absorbent core containing 4 g of cellulosic fibers and 7.5 g of superabsorbent polymer (SAP) and having 2 channels [each channel having a length of around 180 mm and a width of around 8 mm] substantially free of absorbent material and being disposed at each side of the longitudinal central axis (Y-Y). The absorbent core has a basis weight of around 275 g/m².

Table 4 shows the results obtained for embodiments A, B and C described above.

TABLE 4

| | EMBODIMENT A | EMBODIMENT B | EMBODIMENT C |
| --- | --- | --- | --- |
| Total absorption rate after three insults (ml/s) | 2.10 | 4.34 | 3.47 |
| Rewet after three insults. (g) | 20.55 | 13.05 | 8.46 |
| Total distribution length after three insults. (mm) | 235.4 | 262.6 | 276.0 |
| Percentage of use of the absorbent core. (%) | 65 | 73 | 77 |

These results show that the absorption rate of embodiment B is around 20% faster than the absorption rate of embodiment A, and the absorption rate of embodiment C is around 30% faster than the absorption rate of embodiment A. The return of fluids to the surface of the diaper (rewet) of embodiment B is around 35% lower than the rewet of embodiment A and the rewet of embodiment C is around 60% lower than the rewet of embodiment A. The percentage of use of the absorbent core of embodiment B is around 15% greater than the percentage of use of the absorbent core of embodiment A and finally the percentage of use of the absorbent core of embodiment C is around 20% greater than the percentage of use of the absorbent core of embodiment A. Accordingly, the embodiments B and C of the present invention have a better performance than embodiment A of the prior art.

On the other hand, Table 5 shows the results obtained in Embodiment D of the present invention compared with a channeled diaper available on the market (Pampers Confort Sec®).

TABLE 5

|  | EMBODIMENT D | Pampers Confort Sec ® |
|---|---|---|
| Total absorption rate after three insults (ml/s) | 6.89 | 8.88 |
| Rewet after three insults. (g) | 7.02 | 20.78 |
| Total distribution length after three insults. (mm) | 285.6 | 279 |
| Percentage of use of the absorbent core. (%) | 79.33 | 77.5 |

As shown in Table 5, the rewet of Embodiment D is substantially less than the rewet of Pampers Confort Sec®, which keeps the wearer's skin dry and free from irritations; the percentage of use of the absorbent core of the embodiment D shows a better performance in comparison with Pampers Confort Sec®. Finally the absorption rate of Pampers Confort Sec® seems slightly better with respect to embodiment D, however, according to experts in the art, a difference of 2 seconds in absorption rate is not significant for this feature.

The invention claimed is:

1. A disposable absorbent article (100) having a longitudinal direction and a transverse direction, the absorbent article comprising:
   a liquid-pervious topsheet (10),
   a liquid-impervious backsheet (20) and
   an absorbent assembly (30) disposed between the topsheet (10) and the backsheet (20) and having two longitudinal edges (41, 41'), two transverse edges (42, 42'), a wearer-facing surface (43), a garment-facing surface (44), a longitudinal central axis (Y-Y) extending along a length of the absorbent assembly (30) and a transverse central axis (X-X) defining a front portion (45) and a back portion (46), the absorbent assembly (30) comprising:
      an absorbent core (40),
      an upper core wrap (50) and
      a lower core wrap (60),
   wherein the absorbent core (40) comprises absorbent material comprised by a mixture of superabsorbent polymer and cellulosic fibers,
   wherein the absorbent core (40) comprises at least two cavities (70) free of absorbent material having a width (W1) with respect to the transverse central axis (X-X) and a length (L1) with respect to the longitudinal central axis (Y-Y), said cavities (70) being interconnected via at least one connecting line (80) having a width (W2) with respect to the transverse central axis (X-X) and a length (L2) with respect to the longitudinal central axis (Y-Y), the at least one connecting line (80) comprising absorbent material,
   wherein the absorbent core (40) has a first basis weight (bw1) in the zone out of the cavities (70) and the connecting lines (80), and a second basis weight (bw2) in the connecting lines, the first basis weight (bw1) being greater than the second basis weight (bw2), and wherein the upper core wrap (50) and the lower core wrap (60) are permanently attached to each other in the cavities (70).

2. The disposable absorbent article (100) according to claim 1, wherein the at least two cavities (70) are aligned on the longitudinal central axis (Y-Y) of the absorbent assembly (30) and interconnected via at least one longitudinal connecting line (80) substantially parallel to the longitudinal central axis (Y-Y).

3. The disposable absorbent article (100) according to claim 1, wherein the cavities (70) form a pattern, the pattern comprising two rows of at least two cavities (70), the cavities (70) of each row being longitudinally interconnected via at least one longitudinal connecting line (80) substantially parallel to the longitudinal central axis (Y-Y), each row being disposed on each side of the longitudinal central axis (Y-Y).

4. The disposable absorbent article (100) according to claim 1, wherein the cavities (70) are longitudinally spaced from each other by a distance between 5 mm and 250 mm and are transversely spaced from each other by a distance between 5 mm and 250 mm.

5. The disposable absorbent article (100) according to claim 1, wherein the cavities (70) have a shape selected from the group consisting of triangles, squares, rectangles, polygons, circles, ovals, semi-circles, arrow-shapes, crosses, irregular shapes and combinations thereof.

6. The disposable absorbent article (100) according to claim 1, wherein the cavities (70) have an area between 50 mm$^2$ and 2500 mm$^2$.

7. The disposable absorbent article according to claim 1, wherein more than 50% of the total area of the cavities (70) is disposed in the front portion (45) of the absorbent assembly (30).

8. The disposable absorbent article according to claim 1, wherein the ratio (W2/W1) between the transverse width (W2) of the at least one connecting line and the transverse width (W1) of the cavities (70) is at most 1.

9. The disposable absorbent article according to claim 1, wherein the ratio (bw2/bw1) between the second basis weight (bw2) and the first basis weight (bw1) is between 0.25 and 0.95.

10. The disposable absorbent article according to claim 1, wherein the upper core wrap (50) is permanently attached to the lower core wrap (60) in the cavities (70) by means of adhesive, thermal bonding, pressure bonding, mechanical bonding, ultrasonic bonding or combinations thereof.

11. The disposable absorbent article according to claim 1, wherein said disposable absorbent article (100) is selected from the group consisting of baby diapers, adult diapers, baby pants, adult pants, adult incontinence undergarments or pads, sanitary napkins and panty liners.

12. The disposable absorbent article according to claim 1, wherein one or more connecting lines (80) comprise regions having the second basis weight (bw2) and regions having a third basis weight (bw3), wherein the first basis weight (bw1) is greater than the second basis weight (bw2), and the second basis weight (bw2) is greater than the third basis weight (bw3).

* * * * *